United States Patent [19]

Hidano et al.

[11] Patent Number: 5,463,038
[45] Date of Patent: Oct. 31, 1995

[54] METHOD OF PRODUCING KESTOSE CRYSTALS

[75] Inventors: Tetsuhiro Hidano; Hiroyuki Takeda; Masayuki Tsukada; Kazuo Yamamoto; Atsushi Inoue, all of Hokkaido, Japan

[73] Assignee: The Hokuren Federation of Agricultural Cooperatives, Japan

[21] Appl. No.: 940,788

[22] Filed: Sep. 4, 1992

Related U.S. Application Data

[63] Continuation of Ser. No. 738,626, Jul. 31, 1991, abandoned.

[30] Foreign Application Priority Data

Aug. 28, 1990 [JP] Japan ........................... 224312

[51] Int. Cl.$^6$ .............................. C07H 1/06; C07H 3/06; C12P 19/44
[52] U.S. Cl. ................. 536/124; 536/123.1; 536/123.12; 435/74; 435/101
[58] Field of Search ............................ 435/74, 101, 105, 435/124, 127; 536/1.1, 127, 4.1, 123.2, 123.1, 124

[56] References Cited

FOREIGN PATENT DOCUMENTS

| 480519 | 4/1992 | European Pat. Off. . |
| 2572079 | 4/1986 | France . |
| 1568109 | 12/1973 | Germany . |
| 3803339 | 10/1989 | Germany . |
| 60-149596 | 8/1985 | Japan . |
| 2163093 | 6/1990 | Japan . |
| 2249493 | 10/1990 | Japan . |
| 1168596 | 2/1983 | U.S.S.R. . |

OTHER PUBLICATIONS

Jong et al., *ATCC* Catalogue of Funji/Yeasts, 17th ed, 1987, p. 357.
Onions et al. Smith's Intro. Industrial. Mycology, 7th ed, 1981, pp. 58 and 150–152.
Pigman, *The Carbohydrates*, pp. 531–532, 1957.
Horace S Isbell, Carbohydrates in Solution, pp. 186–195, 1973.
Agricultural and Biological Chemistry, vol. 52, No. 5, May 1988 pp. 1181–1187, Hidaka et al.
R. L. Whistler and M. L. Wolfrom, "Mehtos in Carbohydrate Chemistry", 1962 Academic Press, pp. 363–364.
ACTA Crystallographica, vol. B28, No. 1, 15 Jan. 1972, pp. 257–567 Jeffrey et al.
Patent Abstracts of Japan, vol. 14, No. 423 (C–757) (4366) 12 Sep. 1990 & JP A 2 163 093, 22 Jun. 1990.
Beilstein Handbuch der Organischen Chemie; II/IV vol. 17, p. 3820, 1975.

*Primary Examiner*—Irene Marx
*Attorney, Agent, or Firm*—Lorusso & Loud

[57] ABSTRACT

The present invention relates to crystals of 1-kestose which is a fructooligosaccharide, and it is an object of the present invention to provide high-purity 1-kestose crystals having no hygroscopicity and a method of producing the crystals. Methanol is added to an aqueous solution containing as a main ingredient 1-kestose with a purity of 80% or more, and the mixture is then dried. Methanol is further added to the mixture to obtain 1-kestose crystals with a purity of 90% or more. An aqueous solution with a purity of 70% or more is concentrated, and 1-kestose microcrystals are added to the concentrate obtained to separate 1-kestose crystals with a purity of 94 to 99.9%.

3 Claims, 1 Drawing Sheet

METHOD OF PRODUCING KESTOSE CRYSTALS

This application is a continuation of application Ser. No. 07/738,626, filed Jul. 31, 1991, now abandoned.

BACKGROUND OF THE INVENTION

The present invention relates to 1-kestose crystals and a method of producing the same.

1-kestose is a kind of so-called fructooligosaccharides which is a trioligosaccharide having fructose which forms the β-1,2 bonding to the 1-position carbon atom of the fructosyl group of sucrose. 1-kestose is widely distributed in the natural world and contained in burdocks, onions and the like. A fructooligosaccharide containing 1-kestose has recently attracted attention because it has anti-cariosity and it is a bifidobacterium factor which is not digested in a human body.

There has been no existence of 1-kestose prismatic crystals with a purity of 95% or more. A known 1-kestose product is disclosed in the publication of Japanese Patent Laid-Open No. 60-149596 laid open to public in Japan. In the invention disclosed in this publication, a fructooligosaccharide solution containing 60% or more of nystose and a small amount of 1-kestose is concentrated to a solid concentration of 75 to 90%, and seed crystals containing crystal nystose are added to the concentrate obtained and dispersed therein, followed by drying, ripening and grinding to obtain a powder. The powder disclosed in the above publication contains as a main ingredient nystose and does not consist of high-purity 1-kestose crystals it self. In addition, the powder which is obtained by drying the whole syrup obtained and then grinding it contains various ingredients and no 1-kestose crystals which are isolated. The powder as a whole consists of a mixture containing three to five fructooligosaccharides However, the above conventional powder consisting of a fructooligosaccharide mixture containing the above ingredients does not consist of complete crystals and still has hygroscopicity because it contains a plurality of fructooligosaccharides. The powder is thus inconvenient for use in its powder form in foods such as sweetener powders, convenient soup, powder juice drinks and the like, all of which are apt to be easily damaged by moisture and produced on the assumption of long-term preservation. Although it is necessary for removing the above problem to form high-purity crystals having low hygroscopicity, it is laborious to separate the three to five oligosaccharides from each other, which are contained in a fructooligosaccharide mixture solution, by using a carbon sellaite column or the like.

SUMMARY OF THE INVENTION

It is an object of the present invention to provide a method of producing high-purity 1-kestose crystals having no hygroscopicity.

It is another object of the present invention to provide high-purity 1-kestose crystals with no hygroscopicity which can be used in its form in foods which are apt to be easily damaged by moisture.

The present invention exhibits the following effects;

(1) Since high-purity 1-kestose crystals of the present invention have no hygroscopicity, they can be used as additives for foods which are apt to be easily damaged by moisture.

(2) 1-kestose crystals can be produced from a low-purity aqueous solution of 1-kestose with a purity of 70% or more.

(3) Large quantities of high-purity 1-kestose crystals can be produced.

(4) 1-kestose crystals of any desired purity within the range of 94 to 99.9% can be obtained by the production method of the present invention.

The 1-kestose crystals of the present invention are prismatic crystals consisting of 1-kestose with a purity of 95% or more as a main ingredient and nystose and sucrose as impurities.

The 1-kestose crystals of the present invention are produced from a fermentation product derived from microorganisms which belong to the Scopulariopsis genus.

In the method of producing the 1-kestose crystals of the present invention, methanol is added to an aqueous solution containing as a main ingredient 1-kestose with a purity of 80% or more, and, after drying, the crystals separated by adding methanol to the resultant mixture are recovered to obtain 1-kestose crystals with a purity of 90% or more.

In the method of producing the 1-kestose crystals of the present invention, microorganisms belonging to the Scopulariopsis genus are cultured in an aqueous solution containing as a main ingredient 1-kestose with a purity of 80% or more, and 1-kestose crystals with a purity of 90% or more are produced from the aqueous solution.

In the method of producing the 1-kestose crystals of the present invention, an aqueous solution containing as a main ingredient 1-kestose with a purity of 70% or more is concentrated, 1-kestose microcrystals are added to the concentrate obtained, and the crystals separated are recovered to obtain 1-kestose crystals.

BRIEF DESCRIPTION OF THE DRAWINGS

The drawing shows a microphotograph of the structure of 1-kestose crystals.

DETAILED DESCRIPTION OF THE INVENTION

Figure 1:

In the present invention, high-purity 1-kestose crystals can be produced by the methods 1, 2 and 3 below.

In Japanese Patent Laid-Open No. 2-163093 filed by the applicant and laid open to public in Japan, attention is paid to the point that *Scopulariopsis brevicaulis* FERMPS-10438 produces 1-kestose in great abundance, and the conditions for the production of 1-kestose are clarified. This culture is deposited as Deposition No. PERMPS-10438 with FERMENTATION RESEARCH INSTITUTE OF JAPAN.

Application No. 1-70698 (Japanese Patent Laid-Open No. 2-249493) filed by the applicant in Japan discloses a method of purifying a solution containing 1-kestose. The mycological properties of the fungi are disclosed in detail in the specification of Application No. 63-313943 (Japanese Patent Laid-Open No. 2-163093).

The production conditions described in the Japanese Patent Laid-Open No. 2-163093 are as follows:

A medium containing a carbon source, a nitrogen source, inorganic salts and the like is used as a culture medium. Sucrose is used as the carbon source, and the concentration thereof in the medium is 5 to 50%, preferably 10 to 20%. The juice produced during a sugar-manufacturing process, e.g., the juice obtained after removing colloidal substances from raw syrup, the molasses produced in a process of crystallizing sucrose or the like can also used as sucrose. An organic or inorganic nitrogen compound such as a yeast extract, a beef extract, a corn steeping liquor, peptone or the like can be used as the nitrogen source, and the concentration thereof is 1 to 4%, preferably 1.5 to 2.5%. Phosphates, magnesium salts and iron salts, for example, inorganic salts such as potassium phosphate, magnesium sulfate and the like, are further added to the medium in an amount of 0.15 to 1.0%, preferably 0.2 to 0.5%. The pH of the medium is adjusted to 5 to 8, preferably 6.5 to 7.0.

After shaking culture of the fungi for 24 to 48 hours, the fungi are inoculated in the above medium, followed by aerobic jar fermentation at 24° to 40° C. preferably 28° to 30° C., for 24 to 120 hours, preferably 72 to 90 hours. In this case, the whole amount of sucrose may be added as the carbon source at the start of cultivation, or a small amount of sucrose may be added at the start of cultivation so that the remainder is divided into at least one portions and added during cultivation.

An example of the saccharide compositions of the culture solutions obtained by the above cultivation method is described below. When the initial sucrose concentration was 15%, the total amount of saccharides in the culture solution obtained by cultivation using the microorganisms was 11.5%. The whole saccharides consist of 78% of 1-kestose, 3.0% of nystose, 12.3% of fructose, 3.0% of mannitol and 3.7% of sucrose, no glucose being observed. Because the theoretical amount of 1-kestose produced from a 15% sucrose solution is 11%, the yield of 1-kestose in the above case is about 80%. This shows that 1-kestose is obtained with a high yield.

Solid materials such as fungi and the like are removed from the culture solution by solid-liquid separating means such as filtration, centrifugation or the like to obtain a solution containing 1-kestose.

The method of purifying a 1-kestose-containing solution which is disclosed in Patent Application No. 1-70698 (Japanese Patent Laid-Open No. 2-249493) filed by the applicant of the invention is described below.

After the 1-kestose-containing solution obtained by the above cultivation method has been heated to 60° to 80° C., preferably 70° to 75° C., calcium oxide is added thereto. The concentration of calcium oxide added is 0.1 to 0.5% preferably 0.2 to 0.3%. The resultant mixture is then gently agitated for 5 to 10 minutes so as to precipitate most of the colloidal substances which are contained in the 1-kestose-containing solution and which mainly consist of proteins. After the solution has been filtered, the filtrate is heated to 80° to 90° C. preferably 85° C. and calcium oxide is then added thereto over again. At this time, the amount of calcium oxide added may be 0.5 to 2.0%, preferably 1.0 to 1.5%. When the resultant mixture is agitated for 3 to 8 minutes at the above temperature, reducing monosaccharides are degraded, and the remaining proteins which precipitate are removed. Because the pH of the solution is increased to 12 to 12.5 by adding calcium oxide, a large quantity of calcium ions is dissolved in the solution. When the pH of the solution is thus decreased by introducing carbon dioxide, excess calcium ions in the solution are precipitated as calcium carbonate. At this time, carbon dioxide may be introduced in an amount which can decrease the pH value of the solution to 8 or 9. The introduction of carbon dioxide is then stopped so that the precipitates of calcium carbonate are grown. After the precipitates have been removed by filtration, the filtrate is subjected to demineralization using cation and anion exchange resins. The demineralization may be performed under known conditions. If required, the filtrate is then subjected to activated charcoal treatment.

The above-described operation produces a colorless and transparent liquid of $B_x$ 10.5. After the activated charcoal treatment, the liquid is concentrated to obtain a syrup of $B_x$ 70 highly containing 1-kestose and having a saccharide composition consisting of 80 to 90% of kestose, 2 to 5% of nystose, 3 to 8% of mannitol and 2 to 12% of sucrose.

In the present invention, 1-kestose crystals are obtained from the syrup which is obtained by the above purification method and which highly contains 1-kestose with a purity of 80% or more by the following methods (1) to (3):

(1) An appropriate amount of syrup highly containing 1-kestose is dissolved in methanol, and the resultant solution is then dried by vacuum concentration. In order to increase the purity, the concentrate is again dissolved in methanol and then allowed to stand at 1° to 5° C. for 1 to 3 days. The separated-out crystals are separated and collected by a usual method to obtain 1-kestose crystals with a purity of 90 to 97%.

(2) A description will now be given of a method of obtaining 1-kestose crystals from an aqueous solution of at least 70% 1-kestose of a low purity by using as seed crystals the 1-kestose crystals obtained by the method (1).

The 1-kestose crystals obtained by the method (1) are added to an organic solvent such as methanol or the like until they do not dissolve therein, and the resultant solution is shaken together with glass beads to form a suspension of microcrystals. Apart from this, a composition of 1-kestose with a purity of 70% or more is adjusted to °$B_x$ 70 or less, and then placed in a vacuum concentrator in which the composition is concentrated to °$B_x$ 85 at a temperature of 70° to 90° C. After the temperature of the resultant concentrate has been increased to 80° C. or more, an appropriate amount of suspension of the microcrystals is added to the concentrate, followed by curing under agitation, while slowly decreasing the temperature to 65° to 75° C. The separated-out crystals are centrifuged at a temperature of 60° to 80° C. and then dried by a usual method. The purity of the thus-dried 1-kestose crystals is 95 to 99%, and the recovery is 30 to 40%. This method permits the recovery of crystals until the 1-kestose purity of the so-called green syrup remaining after the crystals are separated is 70%. When the recovery of crystals is started from a composition with a 1-kestose purity of 85% or more, at least three times of recovery can be made. As a result, the total recovery is 70% or more.

(3) The thus-obtained 1-kestose crystals are redissolved in water to prepare a mother liquor with a purity of 97% or more, and crystals are obtained by the same method as the method (2). The thus-obtained 1-kestose crystals have a purity of 99.6% or more.

Of the crystals obtained by the above methods, 1-kestose crystals with a purity of 95 to 99% do not absorb moisture even if they are exposed to the outside air for 6 months. In addition, since impurities mainly consist of nystose and a trace of sucrose, the crystals can be used as additives for foods.

The high-purity 1-kestose crystals with a purity of 99.6% or more can be used as extending agents for drugs and used as high-purity samples of anhydrous trisaccharide crystals.

The physicochemical properties of the obtained 1-kestose crystals are shown in Table 1.

TABLE 1

Physicochemical Properties of Crystals

(Purity 99.9%)

| | |
|---|---|
| Melting point | 189–194° C. |
| Specific Rotation | $[\alpha]_D^{20} = +29.5°$–30.5° |
| Crystal form | Prismatic crystal |
| Hygroscopicity | No caking occurs after crystals are allowed to stand at room temperature for 6 months. |

EXAMPLE 1

140 g of mother liquor which was adjusted to $B_x$ 70 and which contained 88% 1-kestose prepared by the above purification method was weighed and then dissolved in methanol. The resultant solution was then dried by an evaporator to obtain a dry substance. The thus-obtained dry substance was dissolved in 300 cc of methanol, and the resultant solution was then allowed to stand at 4° C. for 5 days. The separated-out crystals were filtered off, and the obtained crystals were dried to recover 49 g of 1-kestose crystals. The crystals had a purity of 94%. The crystals contained 5% sucrose and 1% nystose as impurities. The whole crystals were again dissolved in 300 cc methanol, and the resultant solution was then allowed to stand at 4° C. for 2 days. The separated-out crystals were filtered off and then dried to recover 16 g of crystals with a purity of 97%. The results obtained are summarized in Table 2.

TABLE 2

Purity (%) of 1-Kestose Crystals Separated from Methanol

| | 1-Kestose | Sucrose | Nystose |
|---|---|---|---|
| Mother liquor composition | 88 | 9 | 3 |
| Crystal composition | 94 | 5 | 1 |
| Recrystallized composition | 97 | 3 | 0 |

EXAMPLE 2

10 g of 1-kestose crystals with a purity of 97% obtained in Example 1 was shaken in 50 cc methanol together with glass beads to obtain a suspension of microcrystals. On the other hand, a composition of 1-kestose with a purity of 90% was adjusted to $B_x$ 60, and 300 g of the adjusted composition was then placed in a rotary evaporator in which it was concentrated at 80° C. to $B_x$ 85 or more. 1 ml of the suspension was added as seed crystals to the concentrate obtained, and the mixture was then boiled while a flask was rotated at a low speed and then cured while the temperature was gradually decreased to 70° C. The rotation of the flask was stopped when crystals were sufficiently separated-out, and the crystals were then separated by a centrifugal separator kept at 70° to 80° C. The thus-separated crystals were then dried at 60° to 70° C.

The thus-obtained 1-kestose crystals had a purity of 99%, and the recovery was 36%. Crystals were further recovered from the green syrup obtained after recovery. 1-kestose crystals were recovered by the same method as that described above with a purity of 98% and a recovery of 34%. 1-kestose crystals were further recovered from the green syrup remaining after recovery, with a purity of 95% and a recovery of 32%. 72% of 1-kestose could be recovered from the mother liquor by the above procedure. The results obtained are shown in Table 3.

TABLE 3

Result (%) of Recovery of 1-Kestose from Aqueous Solution

| | Purity of 1-Kestose | Recovery | 1-Kestose Content in Green Liquor |
|---|---|---|---|
| Mother Liquor | 90 | — | — |
| First Crystal | 99 | 36 | 85 |
| Second Crystal | 98 | 34 | 78 |
| Third Crystal | 95 | 32 | 69 |

A mixture obtained by mixing the first, second and third 1-kestose crystals obtained by the above method showed a purity of 98% and did not aggregate even if they were allowed to stand in the outside air for 6 months.

EXAMPLE 3

The 1-kestose crystals obtained in Example 2 were redissolved in water to prepare a mother liquor with a purity of 98.6%. High-purity 1-kestose crystals were recovered from the mother liquor by the same method as that employed in Example 2. The first crystals had a purity of 99.9% and the recovery was 41.0% The 1-kestose in the green syrup obtained had a purity of 96.7%.

The 1-kestose crystals obtained from the green syrup, i.e., the second crystals, had a purity of 99.8%, and the recovery was 39.9%. The 1-kestose in the green syrup obtained had a purity of 94.6%.

The 1-kestose crystals obtained from the green syrup had a purity of 91.4%.

The results obtained are shown in Table 4. The total recovery was 78%.

TABLE 4

Result (%) of Recrystallization of 1-Kestose

| | Purity of 1-Kestose | Recovery | 1-Kestose Purity in Green Liquor |
|---|---|---|---|
| Mother Liquor | 98.6 | — | — |
| First Crystal | 99.9 | 41.0 | 96.7 |
| Second Crystal | 99.8 | 39.9 | 94.6 |
| Third Crystal | 99.6 | 39.1 | 91.4 |

The 1-kestose crystals with a purity of 99.9% had a melting point (m.p) of 189° to 194° C. and specific rotation $[\alpha]_D^{20}$ of 29.5° to 30.5°. A microphotograph of the structure of 1-kestose crystals is shown in the drawing.

What is claimed is:

1. A method of producing prismatic 1-kestose crystals having a purity of at least 95% comprising:
    (a) providing a crude aqueous solution of 1-kestose having a purity of at least 70%;
    (b) concentrating said crude aqueous solution to at least °$B_x$ 85;
    (c) heating the concentrated crude aqueous solution to a temperature of at least 80° C.;
    (d) adding a liquid suspension of seed crystals to the concentrated crude aqueous solution at a temperature of at least 80° C.;
    (e) gradually cooling the concentrated crude aqueous solution with added seed crystals to 65°–75° C. to grow said 1-kestose crystals of at least 95% purity; and (f) separating said prismatic 1-kestose crystals of at least 95% purity while maintaining the solution at a temperature of 60°14 80° C.

2. A method in accordance with claim 1, wherein said concentrating is conducted at a temperature of 70°–90° C.

3. A method in accordance with claim 1 further comprising:

dissolving the 1-kestose crystals obtained in step (f) in water to prepare a mother liquor; and repeating steps (b) through (f), using said mother liquor in place of said crude aqueous solution in step (b), to obtain 1-kestose crystals having a purity of at least 99.6%.

* * * * *

UNITED STATES PATENT AND TRADEMARK OFFICE
CERTIFICATE OF CORRECTION

PATENT NO.   : 5,463,038
DATED        : October 31, 1995
INVENTOR(S)  : HIDANO et al It is certified that error appears in the above-indentified patent and that said Letters Patent is hereby corrected as shown below:

On title page, item [30], under "Foreign Application Priority Data": "224312" --2224312--.

Col. 7, line 5, "60°1480°C" should read --60°-80°C--.

Signed and Sealed this

Seventeenth Day of September, 1996

Attest:

BRUCE LEHMAN

Attesting Officer    Commissioner of Patents and Trademarks